(12) United States Patent
Leon et al.

(10) Patent No.: US 6,765,102 B2
(45) Date of Patent: Jul. 20, 2004

(54) WATER-COMPATIBLE CATIONIC EPOXY COMPOUNDS

(75) Inventors: Jeffrey W. Leon, Rochester, NY (US); Paul R. West, Fort Collins, CO (US); Robert E. Mccovick, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 28 days.

(21) Appl. No.: 10/207,720

(22) Filed: Jul. 29, 2002

(65) Prior Publication Data

US 2004/0024173 A1 Feb. 5, 2004

(51) Int. Cl.$^7$ .................. C07D 303/18; C07D 303/22
(52) U.S. Cl. .................. 549/555; 534/604; 564/292; 568/9; 568/10; 568/18
(58) Field of Search .................. 549/555; 534/604; 564/292; 568/9, 10, 18

(56) References Cited

U.S. PATENT DOCUMENTS

| | | | |
|---|---|---|---|
| 3,619,398 A | 11/1971 | Bosso et al. | 204/181 |
| 3,793,278 A | 2/1974 | DeBona | 523/414 |
| 3,839,252 A | 10/1974 | Bosso et al. | 260/29.2 |
| 3,894,922 A | 7/1975 | Bosso et al. | 204/181 |
| 3,928,156 A | 12/1975 | Wismer et al. | 204/181 |
| 3,936,405 A | 2/1976 | Sturni et al. | 260/29.2 |
| 3,937,679 A | 2/1976 | Bosso et al. | 260/29.3 |
| 3,959,106 A | 5/1976 | Bosso et al. | 204/181 |
| 3,962,165 A | 6/1976 | Bosso et al. | 260/29.2 |
| 4,001,101 A | 1/1977 | Bosso et al. | 204/181 |
| 4,001,156 A | 1/1977 | Bosso et al. | 260/29.2 |
| 4,035,275 A | 7/1977 | Sturni et al. | 204/181 |
| 4,038,232 A | 7/1977 | Bosso et al. | 523/410 |
| 4,110,287 A | 8/1978 | Bosso et al. | 260/29.2 |
| 4,208,262 A | 6/1980 | Kubo et al. | 204/181 |
| 4,487,674 A | 12/1984 | Jan Al et al. | 204/181 |
| 5,483,012 A | 1/1996 | Midogohchi et al. | 525/459 |
| 5,602,193 A | 2/1997 | Stark | 523/403 |
| 6,315,882 B1 * | 11/2001 | Sakamoto et al. | 204/489 |

FOREIGN PATENT DOCUMENTS

EP 0 303 182 A1 2/1989

OTHER PUBLICATIONS

USSN 10/207,583 (D–A34938) "Imaging Members With Ionic Multifunctional Epoxy Compounds" by West et al.
USSN 10/207,297 (D–83712) "Water–Compatible Epoxy Compounds Containing Sulfonate Or Thiosulfate Moieties" filed on even date herewith, by J.W. Leon.
ACS Symp. Ser. #114, (1978) (Epoxy Resin Chemistry), pp 57–69, by W. Raudenbesch.
M. Wismer et al., *Journal of Coatings Technology*, "Cathodic Elecrodeposition", vol. 54, No. 688, May 1982, pp 35–44.
P.I. Kordomenos et al., *Journal of Coatings Technology*, "Polymer Compositions For Cationic Electrodepositable Coatings", vol. 54, No. 686, Mar. 1982, pp 33–41.
W.J. Fullen, Paint and Varnish Production, Mar. 1973 "Epoxy Systems", pp. 42–45.
JP Abstract XP–002260519, 1977.
Georg Thieme Verlag Kg:"Onium–Verbindungen" XP–002260520, 2003.

* cited by examiner

*Primary Examiner*—Ba K. Trinh
(74) *Attorney, Agent, or Firm*—J. Lanny Tucker

(57) ABSTRACT

Water-soluble or water-dispersible branched or unbranched cationic epoxy compounds comprise a backbone having covalently attached thereto two or more epoxy moieties and one or more of the same or different organoonium moieties. The backbone comprises at least 25 weight % oxygen.

13 Claims, No Drawings

WATER-COMPATIBLE CATIONIC EPOXY COMPOUNDS

FIELD OF THE INVENTION

This invention relates to novel compositions of matter. More particularly, it relates to cationic epoxy compounds that are water-soluble or water-dispersible and that contain both epoxy and organoonium functionalities. These compounds have utility in heat-sensitive compositions and imaging members such as lithographic printing plates.

BACKGROUND OF THE INVENTION

Epoxy resins represent a very broad class of organic materials that have been found useful in a variety of applications both as bulk materials in and of themselves, as components in composite materials, and as crosslinkers for various polymers. A complete discussion of this multi-billion dollar industry and the huge variety of the chemistry and products involving epoxy resins is provided in a very large amount of literature. See, for example, Flick, Ernest W. *Epoxy Resins, Curing Agents, Compounds, and Modifiers. An Industrial Guide*, Noyes Data Corp.: Park Ridge, N.J., 1987 and Bruins, Paul F. *Epoxy Resins Technology*, Interscience: New York, 1968.

Despite the large amount of available epoxy technology, the overwhelming majority of the uses of epoxy resins involve the preparation of an end product (a bulk material or a coating) that is mechanically tough, resistant to the elements, chemical resistant, and very hydrophobic. Thus, known epoxy resins have not found extensive use in hydrophilic environments in which a net hydrophilic, water-swellable, water-compatible, or readily wettable end product is required. Such uses include bio-compatible materials, aqueous separations media, coatings for lithographic printing plates, and photographic materials.

The current global trend of reducing the amounts of volatile organic compounds permitted in industrial emissions has fueled a continuing interest in the development of useful technology for aqueous-based formulations and coatings for many uses including lithography or computer-to-plate imaging members. Consequently, advances in epoxy resin chemistry have allowed for the use of epoxy resins material in aqueous formulations. The most common strategy for the use of such epoxy resins in aqueous formulations has involved the preparation of aqueous dispersions of hydrophobic, water-insoluble epoxy resins. These dispersions are typically stabilized either by a surfactant or a protective colloid such as poly(vinyl alcohol). Many of these dispersions are sold commercially and a representative example of this type of system is described in U.S. Pat. No. 5,602,193 (Stark). This class of epoxy resins, though formulated in water, are still largely hydrophobic in nature and are not suitable for the applications noted above wherein the target material or coating must be highly wettable or must have a very high water uptake or water compatibility. These resins are also largely incompatible with many water-soluble polymers and multi-phase formulations may result when they are used.

There are a large number of patents describing cationic epoxy resins of the type that are commonly used in electrophoretic coating processes (also knows as electrodeposition coating). Most of these resins, however, contain a mixture of primary, secondary, and tertiary amine groups and are designed such that they can be rendered water-soluble by neutralization with an acid. This property is crucial to their described use, as the production of hydroxide by water reduction at the cathode deprotonates the resin, and the resin is then deposited on a metal surface. This process results in the deposition of a tough, water-insoluble coating on a metal surface in which all of the net charge of the epoxy resin has been destroyed (or neutralized). Examples of cationic amine salt-containing epoxy resins of this type are described for example in U.S. Pat. No. 4,487,674 (Jan Al et al.), U.S. Pat. No. 5,483,012 (Midogohchi et al.), and U.S. Pat. No. 4,208,262 (Kubo et al.).

Epoxy resins used for electrodeposition coating are also broadly described in ACS Symposium Series # 114 (Epoxy Resin Chemistry), pp. 57–69, (Vol. Date 1978), *Journal of Coatings Technology* Vol. 54, No. 688, pp. 35–44 (1982), and *Journal of Coatings Technology* Vol. 54, No. 686, pp. 33–41 (1982).

The solubility of the known epoxy resins used for electrodeposition resins is responsive to pH. There is a desired to have cationic epoxy resins where the solubility is not responsive to pH so there is more latitude in formulation.

U.S. Pat. No. 4,035,275 (Sturni et al.), U.S. Pat. No. 3,839,252 (Bosso et al.), U.S. Pat. No. 3,619,398 (Bosso et al.), U.S. Pat. No. 4,001,156 (Bosso et al.), U.S. Pat. No. 4,110,287 (Bosso et al.), U.S. Pat. No. 4,144,159 (Bosso et al.), U.S. Pat. No. 4,038,166 (Bosso et al.), U.S. Pat. No. 4,081,341 (Christenson et al.), U.S. Pat. No. 3,894,922 (Bosso et al.), U.S. Pat. No. 3,936,405 (Sturni et al.), U.S. Pat. No. 3,962,165 (Bosso et al.), U.S. Pat. No. 3,937,679 (Bosso et al.), U.S. Pat. No. 3,959,106 (Bosso et al.), U.S. Pat. No. 3,928,156 (Wismer et al.), and U.S. Pat. No. 4,001,101 (Bosso et al.) broadly describe epoxy resins that contain both epoxy units and various cationic moieties. The resins preferably are phenolic-based and thus are highly aromatic in nature. This would increase their hydrophobic nature also. These resins, thus, tend to be more hydrophobic in character than is desired for a number of aqueous formulations.

Thus, there is a need for cationic epoxy compounds that are not pH sensitive, can be readily formulated and used in hydrophilic (or aqueous environments), and do not lose their ionic charge in coated form.

SUMMARY OF THE INVENTION

This invention provides a water-soluble or water-dispersible, branched or unbranched compound comprising a backbone having covalently attached two or more epoxy moieties and one or more of the same or different organoonium moieties.

In preferred embodiments, the organoonium moieties are the same or different organoammonium moieties, the same or different organophosphonium moieties, the same or different organosulfonium moieties, or the same or different N-alkylated, positively charged nitrogen-containing heterocyclic moieties, all of which are described in more detail below.

The cationic epoxy compounds of this invention comprise both epoxy units and organoonium moieties that are covalently bound to a backbone. Furthermore, the resins are derived from epoxy-containing backbone precursors that contain at least 25% by weight of oxygen with the remainder being aliphatic hydrocarbons and halogens. These precursor compounds are soluble in water or water-miscible solvents. These cationic epoxy compounds prepared therefrom are useful in the formulation of hydrophilic, water-compatible, water-swellable, or water-wettable coatings and materials and have unexpectedly good solution compatibility with oppositely charged polyelectrolytes. In contrast to the epoxy compounds known in the art, the cationic epoxy compounds of this invention have non-aromatic, oxygen-rich backbones.

DETAILED DESCRIPTION OF THE INVENTION

As most of the compounds of this invention are polydisperse materials having structures that will vary in degree of branching and the degree of functionalization (pendant moieties), it is implied that all descriptions of chemical compounds will apply to the mean, or average structure of each material. Thus, the compounds of this invention can be linear, partially branched to any degree, or fully branched in structure.

The compounds can be obtained from epoxy-containing "precursor compounds" that are branched or unbranched, monomeric, oligomeric, or polymeric compounds comprising at least 25% by weight of oxygen with the remainder of the weight comprising of aliphatic hydrocarbon and residual aliphatic haloalkyl groups (usually chloroalkyl groups). The oxygen atoms are covalently bound within the precursor compound as hydroxy, aliphatic ether, epoxy, or aliphatic ester moieties. Preferably, all non-epoxy moieties are either hydroxy or aliphatic ether groups. Preferably, the percentage of oxygen (by weight) in the precursor compounds is from about 30% to about 50%. It would be apparent to one skilled in the art that the backbones of the epoxy compounds of this invention and the precursor compounds have essentially the same percentage of oxygen. For purposes of this invention, "backbone" refers to the compounds that result if the organoonium compounds are severed from the remainder of the compounds at the carbon-heteroatom bond connecting the organoonium compound and a hydrogen atom is added to provide stoichiometry.

There are no aromatic groups in the backbone of the compounds of this invention (either aromatic carbocyclic or heterocyclic groups). Thus, the compound backbones lack aromaticity.

Furthermore, the precursor compounds are soluble in water or water-miscible solvents such as various alcohols (such as methanol, ethanol, and propanol), tetrahydrofuran, acetonitrile, acetone, glycols (such as ethylene glycol and diethylene glycol), and methyl ethyl ketone.

Preferred precursor compounds are glycidylated carbohydrates and glycidylated polyglycerols. More particularly, representative branched or unbranched precursor compounds used to prepare the compounds of this invention are identified below as Precursors I, II, III, and IV, and Precursors I and II are most preferred:

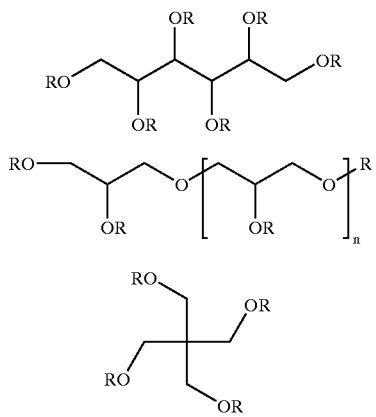

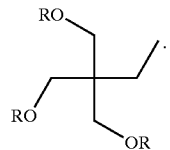

In these compounds, the R groups can be the same or different in each molecule and can be either hydrogen or a glycidyl moiety

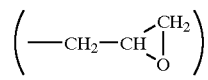

as long as at least two R groups are glycidyl moieties.

Furthermore, Precursors I–IV are also intended to represent branched variations of the simplified linear structures that are illustrated as well as oligomeric species that are formed by intermolecular coupling reactions. It should also be noted that certain methods of preparation of the compounds of this invention result in the presence of haloalkyl residues (in particular, R—$CH_2Cl$ groups) as common byproducts. Though these units are not shown in the simplified structures in FIG. I, their presence in the structures described herein is implied throughout this document and in the descriptions herein.

In Precursor II, n is generally from 1 to 10, and preferably from 2 to 6.

Most preferred precursor compounds include but are not limited to the following materials: glycidyl ethers of sorbitol (Precursor I, sold by Esplit Chemicals under the tradename of CR-5L and by Nagase Chemicals under the tradename of EX-611), of other reduced or non-reduced sugars polysaccharides, or of cellulosics, polyglycerol glycidyl ethers (Precursor II, sold by Nagase Chemicals under the trademark of Denacol® EX-521 and EX-512), pentaerythritol polyglycidyl ethers (Precursor III, sold by Nagase Chemicals under the trademark of Denacol® EX-313 and EX-314), trimethylolpropane polyglycidyl ethers (Precursor IV), glycerol polyglycidyl ethers, poly(ethylene glycol) diglycidyl ethers, glycidyl ethers of poly(vinyl alcohol), and poly(propylene glycol) diglycidyl ether.

The compounds of this invention generally have an average molecular weight of from about 250 to about 1,000,000 daltons. Preferably, the average molecular weight will be from about 250 to about 200,000 daltons, and more preferably, from about 274 to about 20,000 daltons.

It should be noted that, when a nucleophile is reacted with a glycidyl unit on one of the precursor compounds, substitution occurs most commonly at the least hindered (terminal) oxirane methylene carbon. However, multiple substitutions at other positions can also occur. The precursor compounds described herein are intended to include epoxy resins in which nucleophilic substitution has occurred at either position of the oxirane ring.

The compounds of this invention will contain, on average, two or more epoxy moieties and one or more of the noted organoonium moieties described below. It will be noted that where the compounds include two or more organoonium moieties in the same molecule, those organoonium moieties can be the same or different. In addition, the compound may contain pendant hydroxyl groups.

As noted above, the compounds of this invention are water-soluble or water-dispersible. The water-soluble compounds are most preferred. By "water-soluble" is meant that at 60° C., a 2% (by weight) solution of the compound yields a clear solution in water from which no more than 5% of the compound can be recovered by filtration. By "water-dispersible" is meant that at least 2% (by weight) of the compound can be dispersed in water at room temperature without the use of an emulsifying agent to provide a two-phase system that exhibits no observable settling of the solid phase or phase separation after one hour.

The compounds of the present invention may be prepared or used as heterogeneous mixtures, and such mixtures may have both water-soluble and water-dispersible fractions.

Useful organoonium moieties include organophosphonium moieties, organosulfonium moieties, and organoammonium moieties as illustrated in the following Structures V, VI, and VII, respectively:

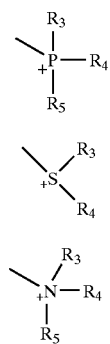

$R_1$, $R_2$, and $R_3$ are independently substituted or unsubstituted alkyl groups having 1 to 12 carbon atoms (such as methyl, ethyl, n-propyl, iso-propyl, hexyl, hydroxymethyl, cyanomethyl, methylenecarboxyalkyl, and dodecyl groups), substituted or unsubstituted carbocyclic or heterocyclic aryl groups having 5 to 10 carbon and/or heteroatoms in the ring (such as phenyl, naphthyl, pyridinyl, tetrahydropyranyl, tetrahydrofuranyl, and p-methylphenyl), and substituted or unsubstituted cycloalkyl groups having from 5 to 10 carbon atoms in the carbocyclic ring (such as 1,3- and 1,4-cyclohexyl groups). Alternatively, any two of $R_1$, $R_2$, and $R_3$ can be combined to form a substituted or unsubstituted heterocyclic ring with the charged phosphorus, sulfur or nitrogen atom, the ring having 4 to 8 atoms in the ring. Such heterocyclic rings include, but are not limited to, substituted or unsubstituted morpholinium, piperidinium, pyrrolidinium, quinuclidine, tetrahydrothiophene, tetrahydrothiopyran, phospholane, and phosphinane groups. The various groups can also include one or more oxy, thio, carbonyl, amido, or alkoxycarbonyl groups.

Preferred $R_1$, $R_2$, and $R_3$ groups are substituted and unsubstituted alkyl groups having 1 to 3 carbon atoms, and methyl and ethyl groups are more preferred. When two or more of $R_1$, $R_2$, and $R_3$ are combined, preferably, they are combined to form 5- or 6-membered rings.

In addition, $R_1$, $R_2$, and $R_3$ can contain additional organoonium groups as substituents. For example, $R_1$, $R_2$, or $R_3$ can be a trimethylammoniomethyl group or a dimethylsulfoniomethyl group, thereby giving a pendant group with a net charge of +2.

Additional organoonium moieties useful in the practice of this invention are N-alkylated positively charged nitrogen-containing heterocyclic moieties that can be represented by the following Structure VIII:

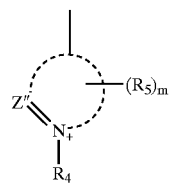

In Structure VIII, $R_4$ is a branched or unbranched, substituted or unsubstituted alkyl group having from 1 to 12 carbon atoms (such as methyl, ethyl, n-propyl, iso-propyl, t-butyl, hexyl, methoxymethyl, benzyl, neopentyl, and dodecyl) or carbocyclic or heterocyclic aryl groups (as defined above). Preferably, $R_4$ is a substituted or unsubstituted, branched or unbranched alkyl group having from 1 to 6 carbon atoms, and most preferably, it is substituted or unsubstituted methyl group.

$R_5$ can be a substituted or unsubstituted alkyl group (as defined above, and additionally a cyanoalkyl group, a hydroxyalkyl group or alkoxyalkyl group), substituted or unsubstituted alkoxy having 1 to 6 carbon atoms (such as methoxy, ethoxy, isopropoxy, oxymethylmethoxy, n-propoxy, and butoxy), halo (such as chloro and bromo), a substituted or unsubstituted carbocyclic or heterocyclic aryl group (as defined above), a substituted or unsubstituted cycloalkyl group having 5 to 8 carbon atoms in the ring (such as cyclopentyl, 1,3-, or 1,4-cyclohexyl, and 4-methylcyclohexyl), or a substituted or unsubstituted non-aromatic heterocyclic group having 5 to 8 atoms in the ring including at least one nitrogen, sulfur, or oxygen atom in the ring (such as pyridyl, pyridinyl, tetrahydrofuranyl, and tetrahydropyranyl). Preferably, $R_5$, is substituted or unsubstituted methyl or ethyl group.

Z" represents the carbon and any additional nitrogen, oxygen, or sulfur atoms necessary to complete the 5- to 10-membered aromatic N-heterocyclic ring that is attached to the polymeric backbone. Thus, the ring can include two or more nitrogen atoms in the ring (for example, N-alkylated diazinium or imidazolium groups), or N-alkylated nitrogen-containing fused ring systems including, but not limited to, substituted or unsubstituted pyridinium, quinolinium, isoquinolinium acridinium, phenanthradinium, and other groups readily apparent to one skilled in the art. Preferred groups of this type are pyridinium groups.

Also in Structure VIII, m is 0 to 6, and it is preferably 0 or 1. Most preferably, m is 0.

The most preferred compounds of this invention include organoonium moieties as represented by the following Structures C, D, E, F, and G in which the organoonium moieties are attached to the compound backbone.

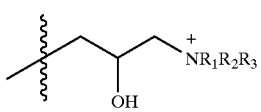

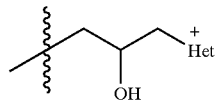

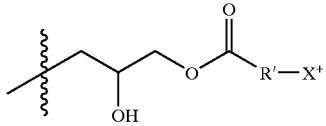

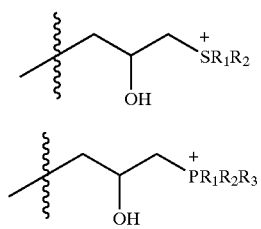

In Structures C–G, R', $R_1$, $R_2$, and $R_3$ are as defined above, "Het" represents an N-alkylated heterocyclic group illustrated in Structure VIII above, and $X^+$ can be any of the organoonium groups described herein.

R' is a divalent unreactive organic linking group capable of connecting the ester unit to the organoonium moiety. Preferably, R' is a substituted or unsubstituted alkylene or cycloalkylene group, and most preferably, it is a substituted or unsubstituted alkylene having 1 to 3 carbon atoms.

While the compounds of this invention will contain one or more or the same or different organoonium moieties and two or more epoxy moieties, preferably, the molar ratio of epoxy moieties to organoonium moieties is from about 19:1 to about 1:19. More preferably, this molar ratio will range from about 4:1 to about 1:4.

The cationic epoxy compounds of this invention are synthesized by chemical modification of the epoxy-containing precursor compounds. Generally, one or more neutral, nucleophilic heteroatom compounds (such as trialkyl amines, dialkyl sulfides, trialkyl phosphines, or nucleophilic, nitrogen-containing heterocycles) and a protic acid (one equivalent of protic acid per equivalent of nucleophilic compound) will be combined with the precursor compound in water, a water-miscible organic solvent, or a mixture thereof. The protic acid can be any organic or mineral acid with a sufficiently non-nucleophilic, non-reactive conjugate base. Hydrochloric acid is a preferred protic acid.

The amount of the neutral, nucleophilic heteroatom compound will be such that complete conversion will afford a compound that will contain more than one epoxy moiety and at least one cationic organoonium moiety per average molecule. Reaction temperatures will generally range from room temperature to 100° C. More commonly, the reaction temperature will be from about 40 to about 60° C. The reactions will typically be run at 5–90% solids. It has been found, however, that at reactions carried out at 10–20% solids and temperatures of less than 60° C. provide optimal conversions (yield) with minimal growth of molecular weight and very little, if any, gelation. The reaction can be conveniently monitored by observing the disappearance of the oxirane protons using proton NMR or by monitoring the disappearance of the nucleophilic heteroatom compound by gas chromatography or ion chromatography. The desired compound can be stored and used in solution in the reaction solvent. Alternately, the solvents can be stripped under vacuum to afford the desired compound resin or the desired compound can be isolated by precipitation into an appropriate non-solvent.

In another embodiment of this invention, the epoxy-containing precursor compound can be reacted via the method described above with a reactant compound containing an organoonium group linked to a carboxylic acid. In this case, a protic acid is not needed. An example of such a reactant compound is betaine hydrochloride. Such a reaction will afford a cationic compound in which the organoonium group is linked to the backbone by an ester linkage to afford a compound that contains pendant moieties identified as Structure E.

It is also possible to prepare and use a mixture of two or more water-soluble or water-dispersible, branched or unbranched compounds of this invention. The compounds would comprise the same or different backbones, each backbone having covalently attached thereto, two or more epoxy moieties and one or more of the same or different organoonium moieties. This mixture of compounds can be prepared by reacting a mixture of precursor compounds noted above with the appropriate amounts and types of reactants, depending upon the reaction scheme that is used. The mixture of compounds can be isolated or used in solution.

The following examples are provided to illustrate the practice of this invention and are not meant to be limiting in any way.

PREPARATIVE EXAMPLE 1

Epoxy Compound 1 Containing 5.3 Epoxy Moieties per Trimethylalkylammonium Moiety DENACOL® EX-521 epoxy resin (10.0 g, Nagase Chemicals) was combined with 75 ml of methanol and 0.96 g of trimethylamine hydrochloride in a 250 ml 2-neck round bottom flask fitted with a reflux condenser and a nitrogen inlet. The reaction mixture was heated for 16 hours at 40° C. at which point analysis no trimethylamine could be detected by headspace gas chromatography. In addition, the $^1$H NMR spectrum showed complete disappearance of the trimethylamine protons and a proportional disappearance of a fraction of the oxirane protons at δ 2–5–2.8 ppm. Proportional growth of a resonance at δ 2.75 ppm was assigned to the $^+$N—CH$_3$ protons. Some of the solvent was removed by rotary evaporation and the resulting compound of this invention was stored as a solution of 21.17% solids in methanol.

PREPARATIVE EXAMPLE 2

Epoxy Compound 2 Containing 4.3 Epoxy Moieties for Every 2.0 Trimethylalkylammonium Moieties The procedure of Example 1 was followed except that 1.91 g of trimethylamine hydrochloride was used. Similar $^1$H NMR trends were observed and were consistent with the proposed structure of the desired compound of this invention. The compound was stored as a solution of 22.45% solids in methanol.

PREPARATIVE EXAMPLE 3

Epoxy Compound 3 Containing 3.3 Epoxy Moieties per 3.0 Trimethylalkylammonium Moieties The procedure of Example 1 was followed except that 2.87 g of trimethylamine hydrochloride was used. Similar $^1$H NMR trends were observed and were consistent with the proposed structure of the desired compound of this invention. The compound was stored as a solution of 24.53% solids in methanol.

PREPARATIVE EXAMPLE 4

Epoxy Compound 4 Containing 1.3 Epoxy Moieties per 5.0 Trimethylalkylammonium Moieties The procedure of Example 1 was followed except that 9.56 g of trimethylamine hydrochloride was used. Similar $^1$H NMR trends were observed and were consistent with the proposed structure of the desired compound of this invention. The compound was stored as a solution of 20.97% solids in methanol.

PREPARATIVE EXAMPLE 5

Epoxy Compound 5 Containing 2.5 epoxy Moieties per 2.4 N-alkylpyridinium Moieties DENACOL® EX-622 epoxy resin (20.0 g, Nagase Chemicals) was combined with 120 g of methanol, 4.2 g of pyridine, and 53.1 ml of 1.0 N methanolic hydrochloric acid in a 250 ml 2-neck round bottom flask fitted with a reflux condenser and a nitrogen inlet. The reaction mixture was heated for 16 hours at 40° C. at which point analysis by $^1$H NMR showed complete disappearance of the pyridine protons in the aromatic region, the appearance of an equimolar amount of pyridinium protons, and the consequent proportional disappearance of a fraction of the oxirane proton resonance at $\delta$ 2–5–2.8 ppm. The resulting compound of this invention was stored as solution of 14.10% solids in methanol.

PREPARATIVE EXAMPLE 6

Epoxy Compound 6 Containing 2.5 Epoxy Moieties per 2.4 α-trimethylammonium Ester Moieties DENACOL® EX-622 epoxy resin (20.0 g, Nagase Chemicals) was combined with 98 ml of methanol, 6.2 g of betaine, and 52.7 ml of 1.0 N methanolic hydrochloric acid in a 250 ml 2-neck round bottom flask fitted with a reflux condenser and a nitrogen inlet. The reaction mixture was heated for 16 hours at 40° C. at which point the cloudy reaction mixture had turned clear. Analysis by $^1$H NMR showed the disappearance of the resonance pertaining to the starting material, the expected decrease in the oxirane proton resonance at $\delta$ 2–5–2.8 ppm, and the appearances of the broad, multi-modal peaks pertaining to the methylene ($\delta$ 4.2–5.5 ppm) and methyl ($\delta$ 2.9–3.2 ppm) resonances of the added α-quaternary ammonium ester function with the expected integrations. The resulting compound of this invention was stored as solution of 15.20% solids in methanol.

PREPARATIVE EXAMPLE 7

Epoxy Compound 7 Containing 2.5 Epoxy Moieties per 2.4 α-trimethylphosphonium Moieties DENACOL® EX-622 epoxy resin (20.0 g, Nagase Chemicals) was dissolved in 40.00 g of methanol in a 500 ml 3-neck round bottom flask fitted with a reflux condenser, nitrogen inlet, and two addition funnels. The first addition funnel was filled with 26.50 ml of 2.0 N HCl in 6.75:1 methanol-water and the apparatus was degassed for twenty minutes under a steady stream of nitrogen. Trimethylphosphine (53 ml, 1.0 molar in tetrahydrofuran) was added to the second addition funnel and the contents of both addition funnels were added to the epoxy solution over 15 minutes. As soon as the addition was completed, the pH of the reaction mixture was found to be 6-7 by pH paper. The reaction mixture was allowed to stir for 16 hours at room temperature, then it was sparged with nitrogen for 16 hours with the effluents passing through a scrubber filled with bleach to remove residual trimethylphosphine. The solvents were removed using rotary evaporation to afford a clear oil that was redissolved in sufficient 1:1 methanol:water to afford 114.92 g of a solution of 20.51% solids that was free of phosphine odors. The $^1$H NMR spectrum of the resulting product showed no residual trimethylphosphine protons, a partial disappearance of a fraction of the oxirane portions at $\delta$ 2.5–2.8 ppm, and proportional growth of a broad doublet at $\delta$ 1.8–2.0 corresponding to the $^+$P—CH$_3$ protons.

COMPARATIVE EXAMPLE

Comparative Epoxy Compound 8 Containing 4 Epoxy Moieties per 4 Trimethylalkylammonium Moieties EPON® SU-8 epoxy resin (20.0 g, Shell Chemicals) was dissolved in 60 ml of acetone containing trimethylamine hydrochloride (neat, 4.24 g) and 4.2 g of water were added to afford a clear reaction solution that was heated at 45° C. After 5 hours, the solution grew cloudy and the pH rose to ~8 and 7.0 g of water was added over the next 3 hours to keep the solution homogeneous. The reaction solution was then allowed to stir at 45° C. overnight to afford a product solution that could be precipitated into tetrahydrofuran or acetone. The starting material had a high solubility in these solvents but was completely insoluble in water. The solvents were removed on a rotary evaporator and the clear oil was redissolved in 60 ml of water to afford a solution having 22.30% solids of a compound outside of the present invention.

PRACTICAL EXAMPLE 1

Solution Compatibility Studies of Cationic Epoxy Resins with Polyelectrolytes of Opposite Charge Solutions [10% (w/w)] of poly(sodium acrylate) (PSA) and poly(sodium styrene sulfonate) (PSSS) in water were prepared. Aliquots of approximately 1 ml of each of the solutions of Epoxy Compounds 1–8 were added to each of the two polymer solutions in order to test the solution compatibility of the possible combinations of each epoxy compound with each of the two anionic polyelectrolytes. The resulting mixtures were shaken vigorously and the clarity of the solutions was observed. In TABLE I below, a result of "C" indicates a completely clear solution resulted and the polymer/epoxy compound combination resulted in high solution compatibility. "SH" indicates that a slightly hazy mixture resulted with no apparent viscosity change, no solid precipitate, and no separation into two layers. "P" indicates that a solid precipitate instantly formed.

TABLE I

| Epoxy Compound | 1 | 2 | 3 | 4 | 5 | 6 | 7 | 8 |
|---|---|---|---|---|---|---|---|---|
| % Oxygen in backbone[1] | 34.98 | 34.98 | 34.98 | 34.98 | 27.53 | 27.53 | 27.53 | 18.3 |
| Organoonium moiety | C | C | C | C | D | E | G | C |
| Eq. per molecule[1a] | 1 | 2 | 3 | 5 | 2.5 | 2.5 | 2.5 | 4 |
| PSA[2] | C | C | C | C | C | SH | SH | P |
| PSSS[3] | C | C | C | C | C | SH | C | P |

[1]Interpolated from combustion analysis results of starting precursor compounds as 100% − (% C + % H + % N + % Cl).
[1a]Equivalent organoonium moiety per epoxy resin.
[2]Mw = 20,000.
[3]Mw = 70,000.

It is commonly known in the art of coating formulation that polyelectrolytes can often be rapidly precipitated from a formulation by the presence of an oppositely charged species. The presence of oppositely charged, multivalent species, such as transition metal ions or other ionomers can lead to very rapid coagulation of a formulation, even at very low concentrations of added multivalent species. This can often be a limit the breadth of formulation options for polymer-based coatings. Clearly, Epoxy Compounds 1–4, which are derived from precursor compounds having 34.98% oxygen content, show a high solution compatibility with both polyelectrolytes. The results for Epoxy Compounds 2–4 are especially unexpected considering the multivalent character of each resin.

Epoxy Compounds 6 and 7, which are derived from a resin having lower oxygen content, showed a slight haze in PSA and Resin 6 showed a slight haze in PSSS. Nonetheless, five printing plates showed the same results. Only vigorous and sustained scrubbing could remove the coatings.

Attempts to formulate an analogous coating using Epoxy Compound 8 failed due to the presence of large amounts of precipitate.

TABLE II

| Coating | Epoxy Compound solution | Wt. resin solution (g) | Polymer solution[2] (g) | Water (g) | Methanol (g) | Surfactant solution[3] (g) | FX-GE-0034 (g) |
|---|---|---|---|---|---|---|---|
| 1 (control) | DENACOL ® EX-521[1] | 0.120 | 7.995 | 7.423 | 7.423 | 0.240 | 1.799 |
| 2 | 1 | 1.360 | 17.989 | 17.879 | 17.879 | 0.576 | 4.317 |
| 3 | 2 | 1.360 | 17.989 | 17.918 | 17.918 | 0.576 | 4.317 |
| 4 | 3 | 1.360 | 17.989 | 17.972 | 17.972 | 0.576 | 4.317 |
| 5 | 6 | 0.789 | 7.995 | 7.089 | 7.089 | 0.240 | 1.799 |

[1]DENACOL ® EX-521 was used neat as received from the manufacturer.
[2]A solution (10.7% in 3:1 methanol:water) of the spiro-quaternary ammonium acrylate switchable polymer

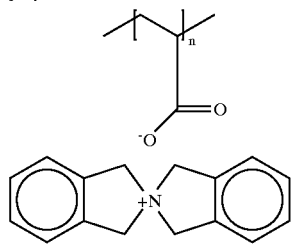

was prepared as described below.
[3]Fluorad FC-135 (obtained from 3M), 5% (w/w) in 2:1 isopropanol:water.
[4]FX-GE-003 is an ethanolic PEG-stabilized carbon black dispersion manufactured by Nippon Shokubai.

no solid precipitates were present, no phase separation was evident, and these resins would be suitable for many types of coating formulations (see Practical Example 2, in which Epoxy Compound 6 is used successfully in a formulation with an anionic polyelectrolyte).

Epoxy Compound 8, which is derived from a known phenolic-based epoxy resin having an oxygen content of 18.1%, produced a gummy precipitate instantly when added to the two polyelectrolytes.

PRACTICAL EXAMPLE 2

Heat-Sensitive Printing Plates Containing Epoxy Compound 1–3

It is known in the art of lithographic printing that it is advantageous for the areas of printing plates that correspond to white (blank) areas of the final prints to have maximum water uptake in order to effectively repel the oil-based inks. In addition, the plates must be physically tough in order to resist abrasion. A tradeoff usually exists between these two desirable properties (physical toughness and hydrophilicity).

Coating compositions for polyelectrolyte-based switchable polymer printing plates were formulated using the components and amounts illustrated in TABLE II below. All formulations produced coherent coatings that were free of flocs and gels. The compositions were coated with a wet coverage of 4.72 cm$^3$/ft$^2$ (51 cm$^3$/m$^2$) on a mechanically grained and anodized aluminum support and dried first in an oven at 80° C. for 5 minutes then for 16 hours at ambient temperature. The toughness of the coatings was tested for wet abrasion resistance by holding the coatings under a stream of warm tap water for several minutes while scrubbing with a lint free cloth (LYM-TECH Purity Wipe®). All The spiro-quaternary ammonium acrylate switchable polymer used in the printing plate formulations described above was prepared in the following manner:

A] Anhydrous ammonia (Aldrich) was bubbled through a rapidly stirring suspension of α,α'-dibromo-o-xylene (26.36 g, Aldrich Chemical) in absolute ethanol (300 ml) for 2.5 hours. The reaction mixture was placed in a freezer for 2 hours and then filtered. The collected white solids were washed once with isopropanol and once with diethyl ether to afford 7.95 g of the quaternary ammonium bromide product as fine, white crystals.

B] A sample (7.39 g) of the product from step A was converted from the bromide to the hydroxide using 5.65 g silver (I) oxide and 70 ml of a 9:1 methanol:water mixture in an analogous manner as used for Polymer 6 (Step B). A solution (14.50 g) of 1.452 meq/g of hydroxide anion was obtained.

C] An aqueous solution [5.02 g of a 25% (w/w)] of polyacrylic acid (Polysciences, MW~90,000) was combined with 14.14 g of methanol and 12.00 g of the solution from step B. A gummy precipitate initially formed and was slowly redissolved over 30 minutes. The resulting polymer was stored as a 16% (w/w) solution in a water/methanol mixture.

The invention has been described in detail with particular reference to certain preferred embodiments thereof, but it will be understood that variations and modifications can be effected within the spirit and scope of the invention.

We claim:

1. A water-soluble or water-dispersible, branched or unbranched compound comprising a backbone having covalently attached thereto two or more epoxy moieties and one or more of the same or different organoonium moieties, said backbone comprising from about 30 to about 50 weight % oxygen and containing no aromaticity.

2. The compound of claim 1 wherein the molar ratio of epoxy moieties to total organoonium moieties is from about 19:1 to about 1:19.

3. The compound of claim 1 wherein the molar ratio of epoxy moieties to total organoonium moieties is from about 4:1 to about 1:4.

4. The compound of claim 1 having an average molecular weight of from about 250 to about 200,000 daltons.

5. The compound of claim 4 having an average molecular weight of from about 274 to about 20,000 daltons.

6. The compound of claim 1 wherein said all non-epoxy, oxygen-containing moieties attached to or within said backbone are either hydroxy, aliphatic ester, or aliphatic ether groups.

7. The compound of claim 6 wherein said all non-epoxy, oxygen-containing moieties attached to or within said backbone are either hydroxy or aliphatic ether groups.

8. The compound of claim 1 wherein said organoonium moieties are the same or different organoammonium moieties, the same or different organophosphonium moieties, the same or different organosulfonium moieties, or the same or different N-alkylated, positively charged nitrogen-containing heterocyclic moieties.

9. The compound of claim 1 wherein said organoonium moieties are the same or different organoammonium or pyridinium moieties.

10. The compound of claim 1 that is derived from a precursor compound that is a glycidylated carbohydrate or glycidylated polyglycerol.

11. The compound of claim 1 that is derived from a precursor compound represented by any of the following Structures I, II, III, and IV:

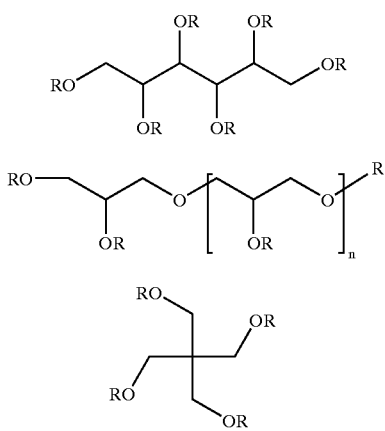

-continued

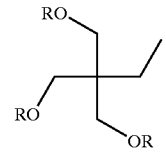

wherein R is hydrogen or

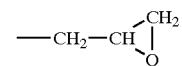

glycidyl moiety, and two or more of the R groups, in each molecule is the glycidyl moiety, and n is 1 to 10.

12. A mixture of two or more water-soluble or water-dispersible, branched or unbranched compounds, each of said compounds comprising the same or different backbones, each backbone having covalently attached thereto two or more epoxy moieties and one or more of the same or different organoonium moieties, the backbones of each of said two or more compounds having from about 30 to about 50 weight % oxygen and containing no aromaticity.

13. A water-soluble or water-dispersible, branched or unbranched compound comprising a backbone having covalently attached thereto two or more epoxy moieties and one or more of the same or different organoonium moieties, said backbone comprising from about 30 to about 50 weight % oxygen and containing no aromaticity, said compound being derived from a precursor compound represented by the following Structure I or II:

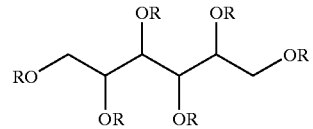

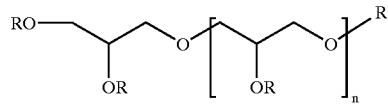

wherein R is hydrogen or

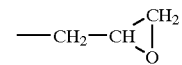

glycidyl moiety, and two or more of the R groups in each molecule is the glycidyl moiety, and n is 1 to 10.

* * * * *